United States Patent [19]

Tsuno

[11] Patent Number: 4,522,113
[45] Date of Patent: Jun. 11, 1985

[54] DEVICE FOR ACCOMMODATING BENDING OF A CABLE
[75] Inventor: Koichi Tsuno, Osaka, Japan
[73] Assignee: Sumitomo Electric Industries, Ltd., Osaka, Japan
[21] Appl. No.: 576,101
[22] Filed: Feb. 2, 1984
[30] Foreign Application Priority Data
Feb. 12, 1983 [JP] Japan .................................. 58-22481
[51] Int. Cl.³ .............................................. F16J 15/18
[52] U.S. Cl. ....................................... 92/113; 92/166; 92/168
[58] Field of Search ................. 92/168 R, 168 B, 166, 92/137, 113; 72/383, 387; 29/DIG. 3

[56] References Cited
U.S. PATENT DOCUMENTS

| 1,818,679 | 8/1931 | Bennett | 72/383 |
| 3,934,450 | 1/1976 | Reed | 72/383 |
| 4,141,235 | 2/1979 | Ishihara | 72/383 |
| 4,351,228 | 9/1982 | Schultz et al. | 92/168 |

FOREIGN PATENT DOCUMENTS

| 49-13033 | 3/1974 | Japan . | |
| 280420 | 11/1969 | U.S.S.R. | 29/DIG. 3 |

OTHER PUBLICATIONS

Olympus Industrial Fiberscopes, date unknown.

Primary Examiner—Paul E. Maslousky
Attorney, Agent, or Firm—Ernest A. Beutler

[57] ABSTRACT

A device for accommodating bending a cable or the like by remote control is proposed. It has a cylinder with a piston rod, and two holders coupled to the cylinder and the piston rod at each end thereof. The holders through which a cable runs are bent by remote control by relative movement between the cylinder and the piston rod.

2 Claims, 6 Drawing Figures

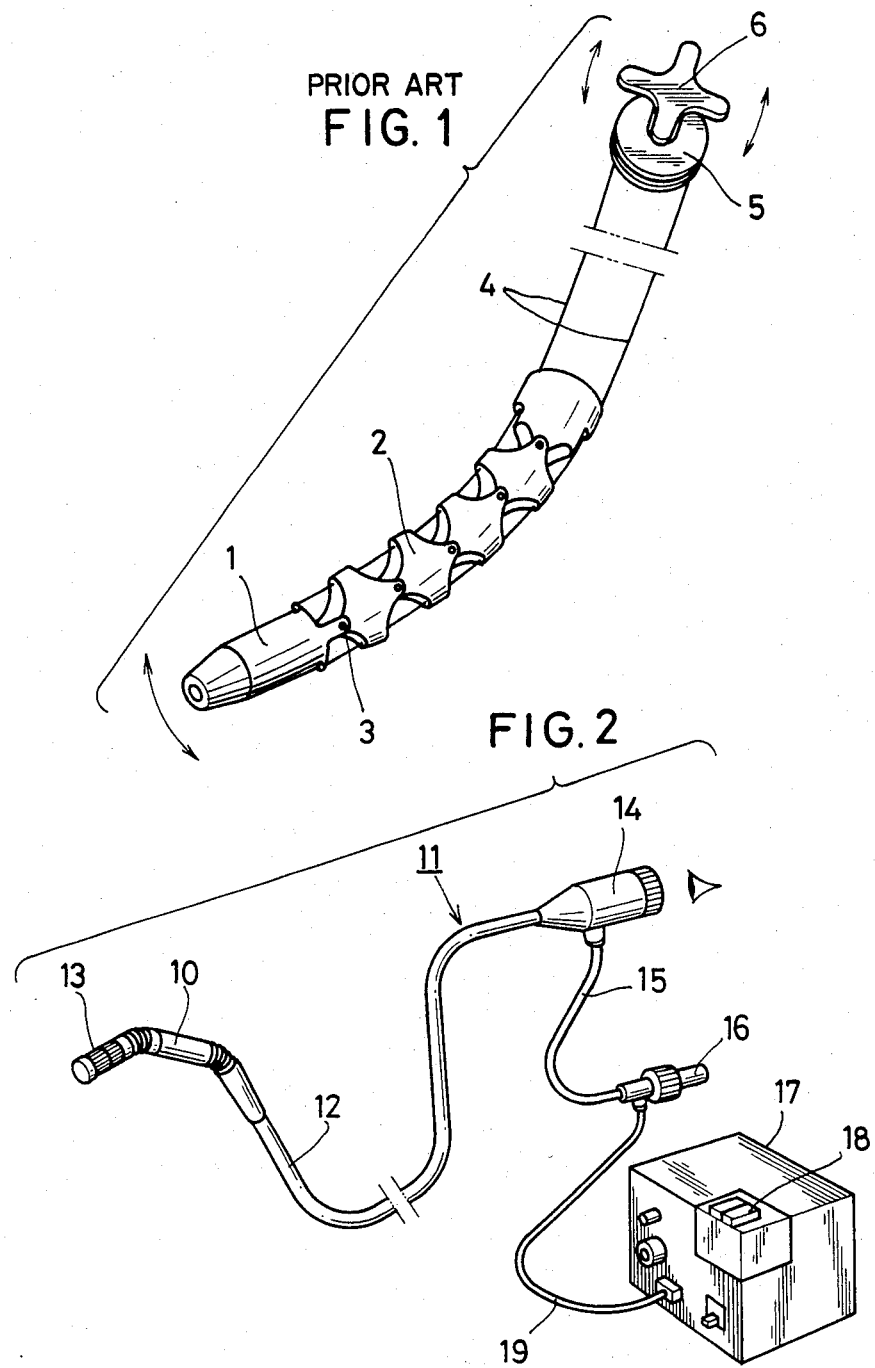

DEVICE FOR ACCOMMODATING BENDING OF A CABLE

BACKGROUND OF THE INVENTION

The present invention relates to a remote-controlled device for accommodating bending an elongated object such as an electric cable, optical fiber cable, and wire.

It is common, as is the case with a gastrocamera, to provide a bending device in the proximity of the camera unit of a fiberscope, and to operate the device from the image-receiving unit so as to bend the camera unit to desired directions. Such a prior art device is shown in FIG. 1, in which a set of links 2 are pivotally connected to one another by means of pins 3 so as to form a flexible ligament extending from a camera unit 1. A pair of wires 4 extend through the links 2 symmetrically with respect to the pins 3. One end of each wire 4 is secured to the camera unit 1, while the other end is wound round a pulley 5 provided on the image-receiving unit. The camera unit 1 can be bent in different directions by turning the pulley 5 with a handle 6.

The above-described prior art device has a disadvantage that the bending angle is limited because the wires 4 stretch and undergo frictional resistance. Especially, the larger the distance from the control unit, the more difficult it is to transmit the movement of each wire from one end thereof to the other.

It is an object of the present invention to provide a remote-controlled bending device which obviates such a disadvantage.

SUMMARY OF THE INVENTION

According to the present invention there is provided a remote-controlled device for bending an elongated object such as a cable, said device comprising a double-acting cylinder having a piston rod slidably mounted in the cylinder, a first holder pivotally coupled to one end of the piston rod so as to be pivotable around a first main coupling pin and pivotally coupled with some play to one end of said cylinder so as to be pivotable around a first auxiliary coupling pin which is parallel to and at a distance from the first main coupling pin, and a second holder pivotally coupled to the other end of the cylinder so as to be pivotable around a second main coupling pin and pivotally coupled with some play to the other end of the piston rod so as to be pivotable around a second auxiliary coupling pin which is parallel to and at a distance from the second main coupling pin.

The piston rod moves relative to the cylinder by difference in the pressure of working fluid fed to the pressure chambers in the cylinder. Consequently, the first and second holders pivot about the first and second main coupling pins, respectively. The angle of the first holder relative to the second holder will be equal to the sum of the angles at which the first and second holders pivot about the respective pins. A larger bending angle can be obtained by incorporating a plurality of such bending devices.

With the above-mentioned object in view and as will become apparent from the following detailed description, the present invention will be more clearly understood in connection with the accompanying drawings, in which:

BRIEF DESCRIPTION OF THE DRAWINGS

FIG. 1 is a partially omitted perspective view of a prior art bending device;

FIG. 2 is a perspective view of a fiberscope incorporating the bending device of the present invention;

DETAILED DESCRIPTION OF THE PREFERRED EMBODIMENT

Figure 3:
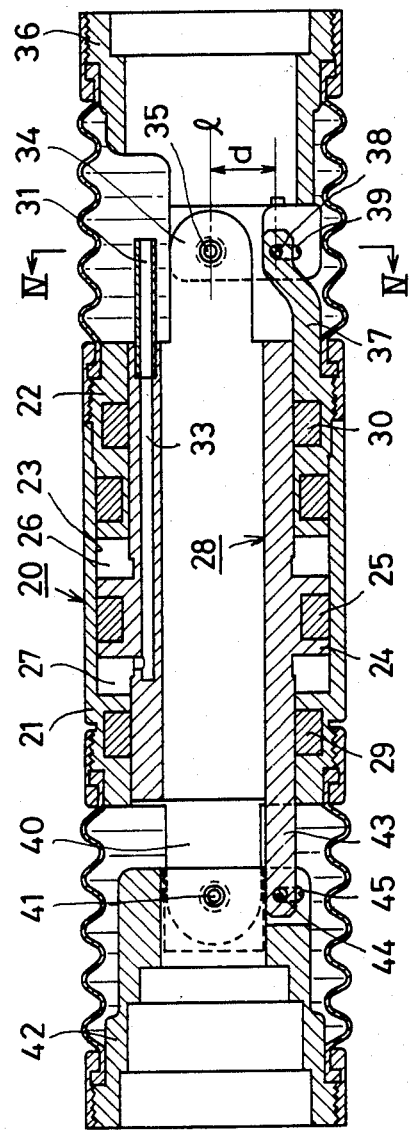
FIG. 3 is a longitudinal sectional view of the bending device.

Referring now to FIG. 2, a bending device 10 in accordance with the present invention is interposed between a transmission unit 12 and a camera unit 13 of a fiberscope 11. An image-receiving unit 14 is connected to the other end of the transmission unit 12. An illumination plug 16 is connected to the image-receiving unit 14 through an optical fiber cable 15. The light supplied from the illumination plug 16 is guided to the camera unit 13 through light guides accommodated in the optical fiber cable 15 and the fiberscope 11.

A valve unit 17 includes a control valve 18. Fluid pressure (oil or air) is applied to the bending device 10 through a hose 19, optical fiber cable 15 and fiberscope 11.

Figure 4:
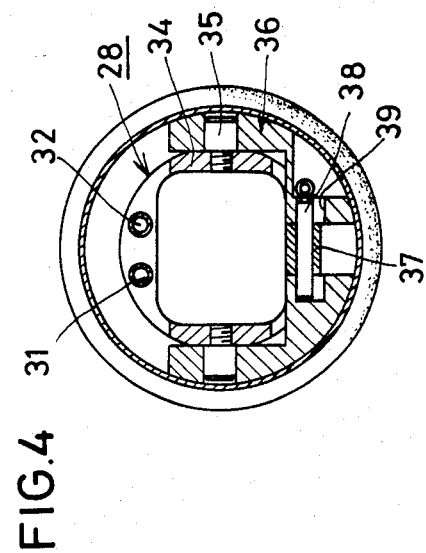
FIG. 4 is a sectional view taken along line IV—IV of FIG. 3.

Referring now to FIGS. 3 and 4, the bending device 10 includes a double-acting cylinder 20 on which the above-described fluid pressure acts. The cylinder 20 is comprised by combining two members 21 and 22 with each other so as to form therebetween an annular recess 23 which is partitioned by a piston 24 provided with a sealing member 25 into two chambers, i.e., a first pressure chamber 26 and a second pressure chamber 27.

A piston rod 28 integral with the piston 24 is in the shape of a tube and is slidably received in the cylinder 20 in sealing engagement with sealing members 29 and 30 provided on the inner surfaces of the cylinder members 21 and 22, respectively. As shown in FIG. 4, the piston rod 28 is provided with inlet ports 31 and 32 to admit the working fluid into the pressure chambers 26 and 27 through respective passages 33.

A projecting portion 34 is provided on one end of the piston rod 28. A first holder 36 is pivotally coupled to the projecting portion 34 of the piston rod through a pair of first main coupling pins 35. The first holder 36 is also pivotally coupled to another projecting portion 37 projecting from the cylinder 20 in the same direction as the projecting portion 34, by means of a first auxiliary coupling pin 38. The first auxiliary coupling pin 38 is parallel with the first main coupling pins 35 and is disposed at a distance of d from the line along which the piston rod 28 acts on the first holder 36. A slot 39 is formed in the first holder 36. The first auxiliary coupling pin 38 passes through the slot 39 so that the first holder 36 is coupled to the cylinder 20 with some amount of play.

A projecting portion 40 is provided on the other end of the cylinder 20. Through a pair of second main coupling pins 41 the second holder 42 is pivotally coupled to the projecting portion 40 of the cylinder. The second holder is also pivotally coupled by a second auxiliary coupling pin 44 to another projecting portion 43 which projects from the piston rod 28 in the same direction as the projecting portion 40. The second auxiliary coupling pin 44 is parallel with the second main coupling pins 41 and is disposed at a predetermined distance from the line along which the cylinder 20 acts on the second holder 42. A slot 45 is formed in the second holder 42. The second auxiliary coupling pin 44 passes through the slot 45 so that the second holder 42 is coupled to the piston rod 28 with some amount of play.

Figure 5:
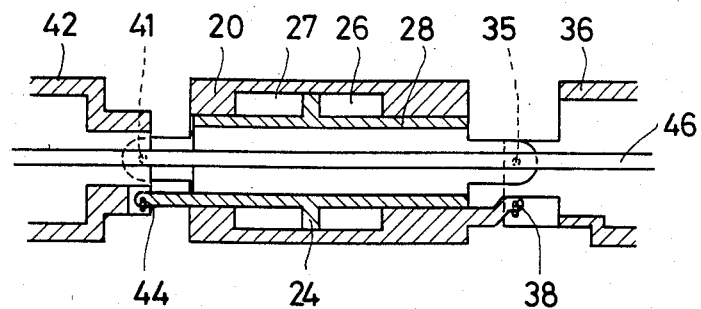
FIGS. 5 and 6 are schematic sectional views illustrating how the bending device operates.
Figure 6:
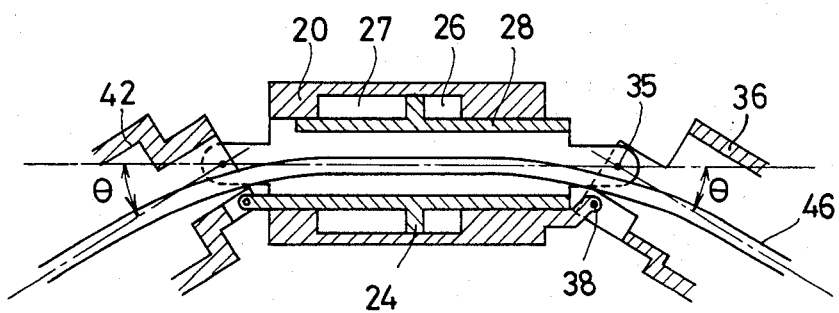

The transmission unit 12 shown in FIG. 2 is connected to the first holder 36, while the camera unit 13 is connected to the second holder 42. As shown in FIGS. 5 and 6, an image fiber 46 or a light guide (or both) passes through the first holder 36, piston rod 28, and second holder 42.

In operation, while the working fluid is supplied under an equal pressure to the first and second pressure chambers 26 and 27, the movement of the piston 24 (hence to the piston rod 28) relative to the cylinder 20 does not occur, so that the first and second holders 36 and 42 are kept in alignment with each other as shown in FIG. 5.

When the control valve 18 in the valve unit 17 is operated to decrease the pressure in the first pressure chamber 26 and increase the pressure in the second pressure chamber 27, this causes the movement of the piston rod 28 relative to the cylinder occurs as shown in FIG. 6. Thus the first holder 36 turns about the first main coupling pins 35 by an angle of $\theta$, because two parallel forces act on the first main coupling pins 35 and the first auxiliary coupling pin 38 in opposite directions and because the pin 38 has play in the slot 39.

Likewise, the second holder 42 turns about the second main coupling pins 41 by an angle of $\theta$. Thus the resultant angle formed between the second holder 42 and the first holder 36 amounts to $2\theta$. This means that in FIG. 2, the camera unit 13 is bent by an angle of $2\theta$ relative to the transmission unit 12.

A bending angle of 60°, which corresponds to the above-described $2\theta$, was obtained in an experiment in which the bending device of the present invention was remote-controlled from a distance of 50 meters from the device.

Although the first and second holders 36 and 42 have been described as the components of the bending device, they may be attachments to the transmission unit 12 and the camera unit 13, respectively.

As mentioned above, the present invention is characterized in that the bending is effected by controlling the pressure of the working fluid fed to two pressure chambers in the cylinder 20 and that the first and second holders 36 and 42 can be tipped by an equal angle at each side of the cylinder. The bending device in accordance with the present invention, therefore, can be used with a device through which an elongated object passes (such as a fiberscope for checking the inside of a pipe or a machine, a robot arm and a guide for laying a cable in piping) so that the device itself and/or the elongated object can be bent thereby at a large angle by remote control.

The movement of the piston rod 28 relative to the cylinder is controlled by the difference in pressures applied to the first and second pressure chambers 26 and 27 of the cylinder 20. Such a pressure difference is unaffected by a change in the ambient temperature. This assures a stable control.

The piston rod 28 in the shape of a tube affords a great convenience because it allows a cable and the like to extend therethrough.

What is claimed:

1. A remote-controlled device for accommodating bending an elongated object such as a cable, said device comprising a double-acting cylinder having a piston rod slidably mounted in said cylinder, a first holder pivotally coupled by a first coupling pin to one end of said piston rod so as to be pivotable around said first coupling pin, said first holder being pivotally coupled with some play to one end of said cylinder by a second coupling pin so as to be pivotable around said second coupling pin, said second coupling pin being parallel to and spaced at a distance from said first coupling pin, and a second holder pivotally coupled to the other end of said cylinder by a third coupling pin so as to be pivotable around said third coupling pin, and said second holder being pivotally coupled with some play to the other end of said piston rod by a fourth coupling pin so as to be pivotable around said fourth coupling pin, said fourth coupling pin being parallel to and offset at a distance from said third coupling pin.

2. The remote-controlled device as claimed in claim 1 wherein said piston rod is in the form of a tube to allow the elongated object to pass therethrough.

* * * * *